United States Patent [19]

Manschot et al.

[11] 4,055,179

[45] Oct. 25, 1977

[54] VALVE FOR URINARY DRAINAGE CONTAINER OR SIMILAR ARTICLE

[75] Inventors: James Gordon Manschot, Mukwonago; Byron L. Mather, Milwaukee, both of Wis.

[73] Assignee: Plastronics, Inc., Milwaukee, Wis.

[21] Appl. No.: 669,874

[22] Filed: Mar. 24, 1976

Related U.S. Application Data

[63] Continuation-in-part of Ser. No. 563,490, March 31, 1975, abandoned.

[51] Int. Cl.$^2$ .............................................. A61F 5/44
[52] U.S. Cl. .................................. 128/275; 128/274; 128/295; 251/333; 251/344; 251/352
[58] Field of Search ............... 128/274, 275, 294, 295, 128/DIG. 24; 137/608–610; 251/342–344, 347–353, 333

[56] References Cited

U.S. PATENT DOCUMENTS

| | | | |
|---|---|---|---|
| 2,358,228 | 9/1944 | Hoof | 137/516.25 |
| 2,538,662 | 1/1951 | Abbott | 128/274 |
| 2,710,626 | 6/1955 | Burdick et al. | 137/498 |
| 3,426,949 | 2/1969 | James | 222/449 |
| 3,707,972 | 1/1973 | Villari et al. | 128/274 |
| 3,823,716 | 7/1974 | Hale | 128/275 |

Primary Examiner—Robert W. Michell
Assistant Examiner—Henry S. Layton
Attorney, Agent, or Firm—Michael, Best & Friedrich

[57] ABSTRACT

A two-piece valve including a first tubular member having a flow passageway therethrough with a tapered valve seat formed at one end of the flow passageway. A second tubular member is provided having a flow passageway therethrough and a valve element mounted in the flow passageway on the axis thereof. The first and second tubular members are slidably telescopically engaged with each other with one end of the first tubular member slidably positioned inside one end of the second tubular member. The valve element of said second tubular member has a tapered valve surface formed thereon adapted to move into and out of sealing engagement with the tapered valve seat of the first tubular member when the tubular members are telescoped axially one inside the other. The taper angles of the valve element and seat are in the "self-holding" category so that when the valve element is firmly seated in the valve seat the parts will be retained in mating engagement without any additional retaining means.

16 Claims, 4 Drawing Figures

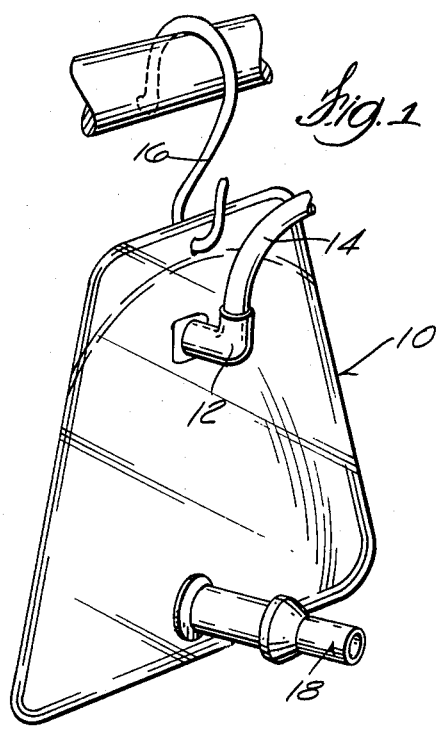
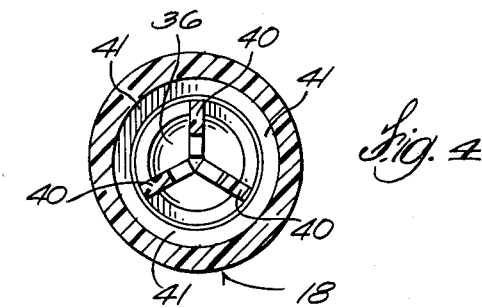
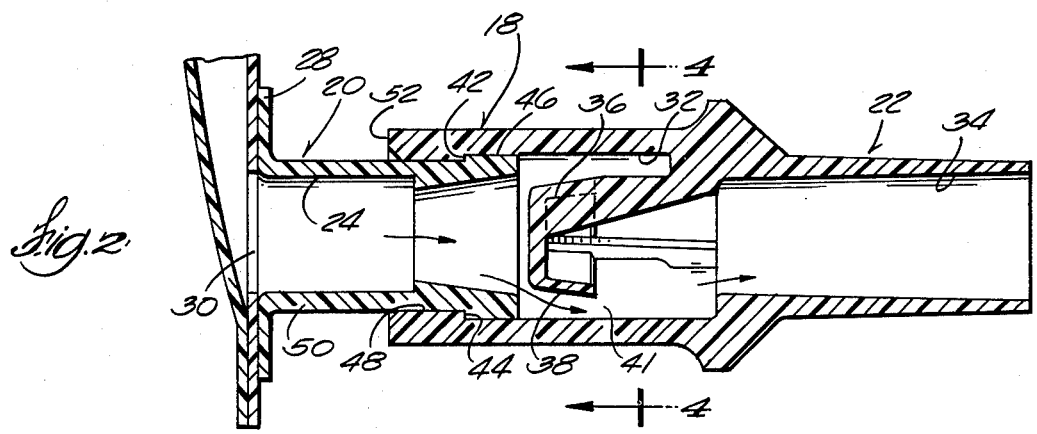
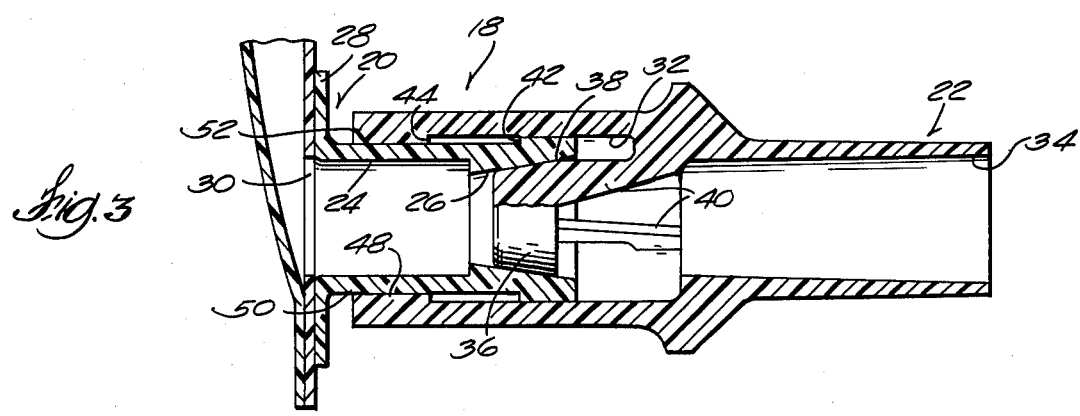

VALVE FOR URINARY DRAINAGE CONTAINER OR SIMILAR ARTICLE

CROSS-REFERENCE TO RELATED APPLICATIONS

This is a continuation-in-part application of application Ser. No. 563,490 filed Mar. 31, 1975 now abandoned.

BACKGROUND OF THE INVENTION

I. Field of the Invention

This invention relates to an improved valve construction and more particularly to a two-piece valve which is opened and closed in response to relative axial slidable movement of the two parts of the valve.

II. Description of the Prior Art

A prior art search directed to the subject matter of this application uncovered the following prior art patents:

| U.S. Pat. Nos. | 234,735 | 1,958,429 |
|---|---|---|
| | 1,423,418 | 2,859,932 |
| | 1,716,802 | 3,219,278 |
| | 1,842,869 | 3,823,716 |

The advantages of the present invention over the prior art known to applicant is that it provides a relatively simple construction which is easily assembled and actuated and which provides a positive shut-off of flow therethrough in closed position and a relatively, free unobstructed flow therethrough when in open position.

SUMMARY OF THE INVENTION

A two-piece valve comprising a first tubular member having a flow passageway means therethrough and a tapered valve seat formed in the flow passageway. A second tubular member is provided which has a flow passageway therethrough and a valve element mounted in such passageway on the axis thereof. A support means is provided for fixedly supporting the valve element in the second tubular member. The first and second tubular members are telescopically engaged with each other with the first tubular member slidably positioned inside the second tubular member. The valve element of the second tubular member has a tapered valve surface formed thereon adapted for movement into and out of sealing engagement with the tapered valve seat of the first tubular member. The tapered valve element and tapered valve seat have self-holding taper angles so that when the valve element is firmly seated in the valve seat the parts will be retained in mating engagement without the need for some type of additional retaining means. The valve element support means has at least one flow passageway therethrough which is blocked when the valve element and valve seat of the two members are in sealing engagement and which is opened when the valve element and valve seat are moved out of sealing engagement.

DESCRIPTION OF THE DRAWINGS

FIG. 1 is a perspective view of a urinary drainage container provided with a drain valve constructed in accordance with the present invention;

FIG. 2 is an enlarged sectional view of the valve in its open position;

FIG. 3 is an enlarged sectional view of the valve in its closed position; and

FIG. 4 is a sectional view taken along line 4—4 of FIG. 2.

DESCRIPTION OF THE PREFERRED EMBODIMENT

While the valve of the present invention has a number of applications, one useful application is as a drainage valve for a flexible urinary drainage container 10 as shown in FIG. 1. Container 10 is made of flexible plastic material preferably polyvinyl chloride and is provided with an inlet fitting 12 having a tube 14 connected thereto for conducting a flow of fluid into the container. Fitting 12 and tube 14 are also preferably made from polyvinyl chloride plastic material. The container 10 can be supported at the bedside of a patient by means of a hook member 16 of suitable design. The valve 18 of the present invention is mounted on the front face of container 10 at the lower portion thereof. The valve, as thus mounted, serves as a means for periodically draining the container of its contents in a manner to be described in detail hereinafter.

As best shown in FIGS. 1-3, valve 18 is comprised of first and second tubular members 20 and 22. Member 20 has a central flow passageway 24 therethrough with an inwardly tapered (frusto-conical surface) valve seat surface 26 formed in one end thereof and an attachment flange 28 formed at the other end thereof. The valve 18 is fastened to container 10 by welding flange 28 to the face of the container with the passageway 24 positioned in alignment with an opening 30 in the face of the container. The parts are welded and securely sealed to each other by the use of a conventional welding procedure using radio frequency energy.

The second tubular member 22 has a central flow passageway 32 therein, an outlet flow passageway 34 and a valve element portion 36 shaped as a frustum of a cone and having a sealing tapered surface 38 thereon. Valve element 36 is supported on the central axis of member 22 by a plurality of angularly spaced relatively thin support arms 40 integrally formed with the valve element 36 and the main body of member 22 providing a plurality of relatively large flow openings 41 between the arms 40. In the preferred embodiment three support arms 40 providing three flow openings 41 are used.

As shown in FIGS. 2 and 3, with the tubular members 20 and 22 in assembled position one end of tubular member 20 is positioned in slidable telescopic engagement inside one end of tubular member 22 so that when tubular members 20 and 22 are moved axially with respect to each other, valve element 36 in member 22 will move into and out of sealing engagement with valve seat surface 26 in member 20. Members 20 and 22 are provided with oppositely facing retaining shoulders 40 and 44 respectively, which serve to retain the two members in assembled position. More specifically, the outside diameter of the end portion 46 of member 20 is the same as the inside diameter of flow passageway 32 of member 22 and the inside diameter of the end portion 48 of member 22 is the same as the outside diameter of the main body portion 50 of member 20. With such arrangement the axial alignment of the parts will be maintained as they are moved between open and shut positions.

In the preferred embodiment tubular members 20 and 22 are of one piece construction and are made by an injection molding process. Preferably member 20 is made of polyvinyl chloride plastic to facilitate the making of the welded connection to container 10. In the preferred embodiment member 22 is made of polyethylene plastic material.

To assemble the two parts of the valve 18 the end portion 48 of member 22 is forced over the outside of end portion 46 of member 20 until the parts assume the position shown in FIG. 2 (with retaining shoulders 42 and 44 in operative position). With the parts positioned as shown in FIG. 2, the valve is in its open position. In such position any liquid in container 10 will drain out through opening 30 and through passageway 24, then past valve seat surface 26, then around and past valve element portion 36 and then through flow openings 41 (as shown by the arrows in FIG. 2) and then out the valve through passageway 34.

To close valve 18 the members 20 and 22 are telescoped axially from the position shown in FIG. 2 to the position shown in FIG. 3. Such axial movement will cause tapered valve surface 38 on valve element 36 in member 22 to be forced into sealing engagement with tapered valve seat 36 of member 20 to thereby shut off flow through the valve. It will be noted that the members 20 and 22 are dimensioned so that the valve will reach its fully closed position (FIG. 3) before the end 52 of member 22 can move into abutting engagement with the face of flange 28 on member 20.

The taper angles of valve surface 38 and valve seat surface 26 are of significance. It is important that such tapers be of the "self-holding" category as opposed to the "self-releasing" category.

With a self-holding taper the valve element 36 when firmly seated in valve seat 26 will be retained in mating engagement with the valve seat without the need for some type of an additional retaining means to hold the parts in closed position.

Generally speaking, to provide this self-holding feature the taper angle of the mating parts must be less than 7 degrees. In the preferred embodiment of this invention the taper angle of valve surface 38 and valve seat surface 26 is approximately 5°.

It will also be noted that as valve element portion 36 moves into sealing engagement with valve seat surface 26, any tendency of the valve seat 26 to be expanded outwardly due to the wedging action of the parts will be restrained not only by the inherent strength of the member 20 but also by the reinforcing action of that portion of member 22 which fits over the outside surface 46 of member 20.

The valve structure set forth above is of relatively simple and inexpensive design and can be easily assembled. The valve operates to provide a substantially unrestricted flow passageway therethrough in open position and a positive shut-off outflow in its closed position.

Finally as previously stated the two-piece valve of the present invention could be usefully employed in applications other than as a drain valve for a flexible urinary drainage container like that described above. For example the valve of the present invention could be usefully employed to control flow in either direction through a length of flexible plastic tubing.

We claim:

1. A two-piece valve comprising:
a first tubular member having a flow passageway means therethrough and a tapered valve seat formed in one end thereof;
a second tubular member having a flow passageway means therethrough and a valve element mounted therein including support means for fixedly supporting said valve element on the axis of said second tubular member, said first and second tubular members being telescopically engaged with each other with said one end of said first tubular member slidably positioned inside one end of said second tubular member, said valve element having a tapered valve surface thereon adapted for sealing engagement with said tapered valve seat of said first tubular member when said tubular members are telescoped axially one inside the other to thereby shut off communication between opposite ends of the valve, said tapered valve element and said tapered valve seat having self-holding taper angles so that when said valve element is firmly seated in said valve seat the parts will be retained in mating engagement without the need for some type of additional retaining means to hold the parts in closed position, said valve element support means having at least one flow passageway therethrough to allow flow through the valve when said valve element is moved out of sealing engagement with said valve seat surface of said first tubular member; and
said two-piece valve further characterized by having the end of said second tubular member within which said first tubular member is telescopically positioned extending over and engaging the outer surface of said first tubular member so that any tendency of the valve seat to be expanded outwardly due to the wedging action of the parts will be restrained not only by the inherent strength of said first tubular member but also by the reinforcing action of that portion of said second tubular member which fits over the outside surface of said first tubular member.

2. A two-piece valve according to claim 1 in which said valve element support means is comprised of a plurality of relatively thin axially spaced support arms which are connected at one end to said valve element member and at the other end to the body of said second tubular member.

3. A two-piece valve according to claim 1 in which said first and second tubular members are provided with oppositely facing retaining shoulders for the purpose of retaining the first and second valve members in assembled position.

4. A two-piece valve according to claim 1 in which said self-holding taper angles are approximately 5°.

5. A fluid flow valve comprising:
a first tubular member having a flow passageway means therethrough and a tapered valve seat formed in said flow passageway means;
a second tubular member having a flow passageway means therethrough and a valve element fixedly mounted therein on the axis of said second tubular member, said first and second tubular members being telescopically engaged with each other with said first tubular member slidably positioned inside said second tubular member, said valve element of said second tubular member having a tapered valve surface thereon adapted for sealing engagement with said tapered valve seat of said first tubular member when said tubular members are telescoped axially one inside the other, said tapered valve element and said tapered valve seat having self-holding taper angles so that when said valve element is firmly seated in said valve seat the parts will be retained in mating engagement without the need for some type of additional retaining means to hold the parts in closed position, said flow passageway means including at least one flow passageway positioned adjacent said valve element which will be blocked when said tapered valve surface of said valve element is moved into sealing engagement with said tapered valve seat of said first tubular member and which will be opened to allow flow through the valve when said valve element is moved out of sealing engagement with said valve seat surface; and said fluid flow valve further characterized by having the end of said second tubular member within which said first tubular member is telescopically positioned extending over and engaging the outer surface of said first tubular member so that any tendency of the valve seat to be expanded outwardly due to the wedging action of the parts will be restrained not only by the inherent strength of said first tubular member but also by the reinforcing action of that portion of said second tubular member which fits over the outside surface of said first tubular member.

6. A fluid flow valve according to claim 5 in which said valve element of said second tubular body is supported on the axis of said second tubular member by a support means, said flow passageway of said flow passageway means located in said valve element support means.

7. A fluid flow valve according to claim 6 in which said valve element support means is comprised of a plurality of relatively thin axially spaced support arms which are connected at one end to said valve element member and at the other end to the body of said second tubular member to thereby provide a plurality of flow passageways between said axially spaced support arms.

8. A fluid flow valve according to claim 5 in which said first and second tubular members are provided with oppositely facing retaining shoulders for the purpose of retaining the first and second valve members in assembled position.

9. A fluid flow valve according to claim 5 in which said self-holding taper angles are approximately 5°.

10. The combination of a flexible urinary drainage container and a drainage valve therefor comprising:
a sealed container having a drainage opening in the bottom portion thereof;
a two-piece drainage valve attached to said container for controlling the flow from said container through said drainage opening; said two-piece valve comprising a first tubular member having a flow passageway means therethrough and a tapered valve seat formed in said flow passageway means, and a second tubular member having a flow passageway means therethrough and a valve element fixedly mounted therein on the axis of said second tubular member, said first and second tubular members being telescopically engaged with each other with said first tubular member slidably positioned inside said second tubular member, said valve element of said second tubular member having a tapered valve surface thereon adapted for sealing engagement with said tapered valve seat of said first tubular member when said tubular members are telescoped axially one inside the other, said tapered valve element and said tapered valve seat having self-holding taper angles so that when said valve element is firmly seated in said valve seat the parts will be retained in mating engagement without the need for some type of additional retaining means to hold the parts in closed position, said flow passageway means of said first tubular member including at least one flow passageway positioned adjacent said valve element which will be blocked when said tapered valve surface of said valve element is moved into sealing engagement with said tapered valve seat of said first tubular member and which will be opened to allow flow through the valve when said valve element is moved out of sealing engagement with said valve seat surface; and said combination further characterized by having the end of said second tubular member within which said first member is telescopically positioned extending over and engaging the outer surface of said first tubular member so that any tendency of the valve seat to be expanded outwardly due to the wedging action of the parts will be restrained not only by the inherent strength of said first tubular member but also by the reinforcing action of that portion of said second tubular member which fits over the outside surface of said first tubular member.

11. The combination according to claim 10 in which said valve element of said second tubular body is supported on the axis of said second tubular member by a support means with said flow passageway of said flow passageway means located in said valve element support means.

12. The combination according to claim 11 in which said valve element support means is comprised of a plurality of relatively thin axially spaced support arms which are connected at one end to said valve element member and at the other end to the body of said second tubular member to thereby provide a plurality of flow passageways between said axially spaced support arms.

13. The combination according to claim 10 in which said first and second tubular members are provided with oppositely facing retaining shoulders for the purpose of retaining the first and second valve members in assembled position.

14. The combination according to claim 10 in which said self-holding taper angles are approximately 5°.

15. A two-piece valve comprising:
a first tubular member of deformable plastic material having a flow passageway means therethrough and a tapered valve seat formed in one end thereof; and
a second tubular member of deformable plastic material having a flow passageway means therethrough and a valve element mounted therein including support means for fixedly supporting said valve element on the axis of said second tubular member, said first and second tubular members being telescopically engaged with each other with said one end of said first tubular member slidably positioned inside one end of said second tubular member, said valve element having a tapered valve surface thereon adapted for sealing engagement with said tapered valve seat of said first tubular member when said tubular members are telescoped axially one inside the other to thereby shut off communication between opposite ends of the valve, said tapered valve element and said tapered valve seat having self-holding taper angles so that when said valve element is firmly seated in said valve seat the parts will be retained in mating engagement without the need for some type of additional retaining means to hold the parts in closed position, said tapered valve seat effectively extending beyond the end of said valve element when said valve element is seated in said valve seat so that as the material of said first and second members becomes deformed slightly due to repeated actuation of the value members between open and closed positions the valve element will continue to firmly seat in said valve seat, said valve element support means having at least one flow passageway therethrough to allow flow through the valve when said valve element is moved out of sealing engagement with said valve seat surface of said first tubular member.

16. The combination of a flexible urinary drainage container and a drainage valve therefor comprising:

a sealed container having a drainage opening in the bottom portion thereof;

a two-piece drainage valve attached to said container for controlling the flow from said container through said drainage opening; said two-piece valve comprising a first tubular member made of a deformable plastic material having a flow passageway means therethrough and a tapered valve seal formed in said flow passageway means, and a second tubular member made of a deformable plastic material having a flow passageway means therethrough and a valve element fixedly mounted therein on the axis of said second tubular member, said first and second tubular members being telescopically engaged with each other with said first tubular member slidably positioned inside said second tubular member, said valve element of said second tubular member having a tapered valve surface thereon adapted for sealing engagement with said tapered valve seat of said first tubular member when said tubular members are telescoped axially one inside the other, said tapered valve element and said tapered valve seat having self-holding taper angles so that when said valve element is firmly seated in said valve seat the parts will be retained in mating engagement without the need for some type of additional retaining means to hold the parts in closed position, said tapered valve seat effectively extending beyond the end of said valve element when said valve element is seated in said valve seat so that as the material of said first and second members becomes deformed slightly due to repeated actuation of the valve members between open and closed positions the valve element will continue to firmly seat in said valve seat, said flow passageway means of said first tubular member including at least one flow passageway positioned adjacent said valve element which will be blocked when said tapered valve surface of said valve element is moved into sealing engagement with said tapered valve seat of said first tubular member and which will be opened to allow flow through the valve when said valve element is moved out of sealing engagement with said valve seat surface.

* * * * *